US009939462B2

(12) United States Patent
Glocker

(10) Patent No.: US 9,939,462 B2
(45) Date of Patent: Apr. 10, 2018

(54) PROBE FOR MEASURING BIOMOLECULES BY MEANS OF ELECTROCHEMICAL IMPEDANCE SPECTROSCOPY

(71) Applicant: Kimal plc, Uxbridge, Middlesex (GB)

(72) Inventor: Raymond Glocker, Aschaffenburg (DE)

(73) Assignee: Kimal PLC, Uxbridge (GB)

( * ) Notice: Subject to any disclaimer, the term of this patent is extended or adjusted under 35 U.S.C. 154(b) by 857 days.

(21) Appl. No.: 14/278,793

(22) Filed: May 15, 2014

(65) Prior Publication Data

US 2015/0015276 A1 Jan. 15, 2015

(30) Foreign Application Priority Data

May 15, 2013 (DE) ........................ 10 2013 008 243

(51) Int. Cl.
*G01N 21/00* (2006.01)
*G01R 1/067* (2006.01)
(Continued)

(52) U.S. Cl.
CPC ............ *G01R 1/067* (2013.01); *A61B 5/0537* (2013.01); *A61B 5/0538* (2013.01);
(Continued)

(58) Field of Classification Search
None
See application file for complete search history.

(56) References Cited

U.S. PATENT DOCUMENTS 5,596,150 A * 1/1997 Arndt ........................ G01F 1/64
73/861.12
5,603,333 A 2/1997 Konings
(Continued)

FOREIGN PATENT DOCUMENTS

EP 1319943 A2 6/2003
WO 8809808 A2 12/1988
WO 9721094 A1 6/1997

OTHER PUBLICATIONS

Moosavi P. et al, "Directivity of Microstrip Ring Antennas and Effects of Finite Ground Plane on the Radiation Parameters", Antennas and Propagation Society International Symposium, 1998, New York, NY, IEEE, US, vol. 2, Jun. 21, 1998, pp. 672-675, XP010292246, ISBN 978-0-7803-4478-5.
(Continued)

*Primary Examiner* — Jill A Warden
*Assistant Examiner* — Brittany I Fisher
(74) *Attorney, Agent, or Firm* — Grossman Tucker Perreault & Pfleger, PLLC

(57) ABSTRACT

A probe (1) for measuring biomolecules by means of electrochemical impedance spectroscopy is proposed, having a distal end (2) and a proximal end (3), wherein the probe (1) has the following structure in a cross-section oriented transversely to its longitudinal extent: a base layer (4) of an insulating material, on a first side of the base layer (4) at least one layer (5, 6) of a conducting material, on a second side of the base layer (4), which is remote from the first side of the base layer (4), at least one layer (8) of a conducting material, and on the side of the layers of conducting material that is remote from the base layer (4), on the outside, in each case an outer layer (15) of an insulating material, wherein further the at least one layer (5, 6) of a conducting material on the first side of the base layer (4) is formed into an annular conductor structure (9) in the region of the distal end (2) of the probe, wherein the annular conductor structure (9) is followed proximally by at least one elongate conductor (10) which is in the form of a feed line for the annular conductor structure and extends to the proximal end (3) of the probe (1), and wherein the at least one layer (8) of a conducting material on the second side of the base layer (4) covers the predominant part of the base surface of the base layer (4), wherein the layer (8) of a conducting material on
(Continued)

the second side of the base layer (4) has in the region of the distal end (2) of the probe (1) a polygonal hole (13) which is arranged concentrically to the annular conductor structure (9).

24 Claims, 5 Drawing Sheets

(51) Int. Cl.

| | | |
|---|---|---|
| G01R 27/02 | (2006.01) | |
| A61B 5/053 | (2006.01) | |
| A61B 5/145 | (2006.01) | |
| G01N 27/02 | (2006.01) | |

(52) U.S. Cl.
CPC .......... *A61B 5/14546* (2013.01); *G01R 27/02* (2013.01); *G01N 27/026* (2013.01); *G01N 2800/26* (2013.01)

(56) References Cited

U.S. PATENT DOCUMENTS

| | | | |
|---|---|---|---|
| 5,852,229 A | 12/1998 | Josse et al. | |
| 5,945,832 A | 8/1999 | Harvey, III et al. | |
| 6,766,191 B1 | 7/2004 | Billings et al. | |
| 7,432,068 B2 | 10/2008 | Frey et al. | |
| 7,803,628 B2 | 9/2010 | Glocker | |
| 2005/0112544 A1 | 5/2005 | Xu et al. | |
| 2006/0240248 A1* | 10/2006 | Kanai | G03G 5/10 428/336 |
| 2007/0167022 A1* | 7/2007 | Tsai | G01R 1/07371 438/712 |
| 2008/0158066 A1 | 7/2008 | Yu et al. | |
| 2009/0284275 A1* | 11/2009 | Chou | G01R 1/06755 174/68.1 |
| 2011/0003166 A1* | 1/2011 | Brehm | B44F 1/02 428/596 |
| 2011/0189783 A1* | 8/2011 | Andrew | B82Y 20/00 436/149 |
| 2011/0287977 A1* | 11/2011 | Cai | G01N 27/3278 506/13 |
| 2012/0061257 A1* | 3/2012 | Yu | A61B 5/02007 205/792 |
| 2012/0288948 A1* | 11/2012 | Lindsay | G01N 33/48721 436/94 |
| 2013/0106457 A1* | 5/2013 | Lee | G01R 1/06738 324/755.11 |

OTHER PUBLICATIONS

Pirinoli P. et al, "Full-Wave Spectral Analysis and Design of Annular Patch Antenna with Electromagnetically Coupled Microstrip Feed Line", IEEE Transactions on Antennas and Propagation, IEEE Service Center, Piscataway, NJ, vol. 52, No. 9, Sep. 1, 2004, pp. 2415-2423, XP011118435, ISSN: 0018-926X.

Suselbeck T. et al, "In Vivo Intravascular Electric Impedance Spectroscopy Using a New Catheter with Integrated Microelectrodes", Basic Research in Cardiology, vol. 100, No. 1, Nov. 24, 2004, pp. 28-34, XP055142500, ISSN:0300-8428.

Bahl I.J. et al, "A New Microstrip Radiator for Medical Applications", IEEE Transactions on Microwave Theory and Techniques, IEEE Service Center, Piscataway, NJ, vol. MTT-28, No. 12, Dec. 1, 1980, pp. 1464-1468, XP001388264, ISSN: 0018-9480.

Chen H-M., "A Circular Polarized Annular Ring Microstrip Antenna", IEEE Antennas and Propagation Society International Symposium 1998, Atlanta, GA, Jun. 21-26, 1998, vol. 3, pp. 1352-1355, ISBN: 0-7803-4478-2.

English language summary of International Standard CEI IEC 250, First Edition, 1969, pp. 1-7.

Marrocco, Gaetano, "The Art of UHF RFID Antenna Design: Impedance-Matching and Size-Reduction Techniques", IEEE Antennas and Propagation Magazine, vol. 50, No. 1, Feb. 2008, pp. 66-79.

* cited by examiner

PROBE FOR MEASURING BIOMOLECULES BY MEANS OF ELECTROCHEMICAL IMPEDANCE SPECTROSCOPY

The invention relates to a probe for measuring biomolecules by means of electrochemical impedance spectroscopy.

It is known to determine the concentration of haematocrit in the blood by means of electrochemical resonance spectroscopy. This is carried out with excitation at frequencies in the region of 100 kHz.

From DE 100 15 818 A1 there is known a biosensor and a method for detecting macromolecular biopolymers, in which an impedance measurement is carried out at 50 mV with probe molecules immobilised on electrodes in order to determine DNA strands. A first and a second electrode are thereby to be divided into a plurality of electrode segments that are electrically insulated from one another, whereby it is to be possible for arbitrarily chosen electrode segments, independently of one another, to be coupled electrically so that an effective electrode surface is adjustable in terms of its size independently of the chosen electrode segments.

From WO 97/21094 A1 there is known an impedance measuring system for identifying molecular structures in a sample solution. The described sensor comprises an insulating layer having a plurality of spaced channels in substantially the same direction. A side wall of each channel and the upper side of the insulating substrate are coated with metal to form an electrode. The test solution is to be located inside and between the channels.

From U.S. Pat. No. 5,945,832 there is known a device and a method for measuring electrical properties of an electrically conductive molecule. To that end, a first metal contact surface is provided with an insulating layer, and a second contact surface is applied to the insulating layer so that an edge forms at a molecular distance from the first contact surface. A conductive organic molecule having a metal binding group is connected to the metal contacts.

From EP 1 319 943 A2 there is known an impedance sensor for analytes in liquid solution. This is to have two spaced, in particular flat, conductors. An analyte to be studied is introduced into a measuring chamber between the conductors, which changes the impedance of the sensor.

In principle, it is known that frequency-dependent measurements in the range from a few kHz to about 100 GHz provide information about dynamic processes at molecular level. At only a few tens of kHz, the skin effect and protection from high-frequency interference require the use of shielded coaxial cables. This requirement is not a problem for extracorporeal impedance measuring cells, as are described, for example, in DE 103 21 099 A1 or in U.S. Pat. No. 7,803,628, in contrast to invasive probes, where the outside diameters of commercial coaxial cables, which are dictated by the available dielectrics, already prohibit use in catheters, for example. Although some known impedance measuring cells already measure more than haematocrit, in some cases even in vivo, as described, for example, in U.S. Pat. No. 6,766,191 by finger clip through the skin, or by means of annular electrodes on a catheter, see U.S. Pat. No. 5,603,333, the measurement of biomolecules such as proline has hitherto been reserved for scientific works, which function only in laboratory devices, because, unlike the measurement of blood cells by impedance spectroscopy in the higher kHz range, frequencies in the higher MHz range are required in the case of biomolecules. Conventional catheter cables, such as are used, for example, for thermistors in thermodiulation catheters, are not suitable for such HF measurements.

There is therefore a need for improved probes for measuring biomolecules by means of electrochemical impedance spectroscopy.

The object is achieved according to the invention by a probe for measuring biomolecules by means of electrochemical impedance spectroscopy, having a distal end and a proximal end, wherein the probe has the following structure in a cross-section oriented transversely to its longitudinal extent: a base layer of an insulating material, on a first side of the base layer at least one layer of a conducting material, on a second side of the base layer, which is remote from the first side of the base layer, at least one layer of a conducting material, and on the side of the layers of conducting material that is remote from the base layer, on the outside, in each case an outer layer of an insulating material, wherein further the at least one layer of a conducting material on the first side of the base layer is formed into an annular conductor structure in the region of distal end of the probe, wherein the annular conductor structure is followed proximally by at least one elongate conductor which is in the form of a feed line for the annular conductor structure and extends to the proximal end of the probe, and wherein the at least one layer of a conducting material on the second side of the base layer covers the predominant part of the base surface of the base layer, wherein the layer of a conducting material on the second side of the base layer has in the region of the distal end of the probe a polygonal hole which is arranged concentrically to the annular conductor structure.

By means of the probe according to the invention it is possible to detect biomolecules, in particular lactate, in blood, also in vivo, by excitation in the frequency range of from approximately 70 MHz to approximately 165 MHz. In particular, it is possible to detect changes in the lactate level. An elevated lactate level is an indicator of sepsis. It is thereby possible, for example, to detect the onset of sepsis in an intensive care patient long before it would be possible with the methods conventional hitherto. It is thus possible for the medical staff to take countermeasures in good time and thereby substantially reduce mortality as a result of sepsis during intensive care treatment.

Contrary to expectations from scientific publications and the known prior art, the structure according to the invention has been found to be very broad-banded, so that a surprisingly high specificity of the probe is achieved.

A probe according to the invention can be produced with such small dimensions that it can be used in vivo. To that end, the probe is inserted into a lumen of a catheter fitted invasively. The probe can also be immersed in vitro into a sample container or brought up to the outside of a sample container. Embedding in test strips is also possible. The probe can further be used in extracorporeal containers connected to the circulatory system of a patient, for example during blood purification or use of a heart-lung machine. The probe according to the invention has been found to be so effective that measurements can even be carried out through thin plastics walls, such as catheter walls.

In particular, it is possible with the structure according to the invention to use a probe according to the invention in the side lumen of multi-lumen catheters, such as are frequently used for the care of intensive care patients.

Because the measurement with a probe according to the invention is carried out from a closed catheter lumen and therefore does not come into contact with the patient's blood, multiple use of the probe is even possible.

Advantageously, each of the layers of a conducting material is embedded in an insulating material and/or the conducting material is a copper alloy and preferably each layer consists of a first ply of a copper film and a second ply applied to the first ply by galvanic deposition.

In terms of manufacture, it is advantageous if the insulating material of the base layer is the same material as that of the outer layers and/or of the embedding material of the layers of a conducting material. In order to keep signal attenuation in the probe as low as possible, it is advantageous if the material of the base layer is a material having a dielectric constant of less than 3.7.

Polyimide has been found to be a particularly suitable material.

For good radiation characteristics, it is advantageous if the polygonal hole is at least sufficiently large that the annular conductor structure is not covered by the conducting material on the second side of the base layer that surrounds the hole, wherein the largest diameter of the hole is preferably not more than 1.5 times the largest diameter of the annular conductor structure.

For particularly broad-banded radiation, and accordingly for high specificity, it is advantageous if the polygonal hole has from four to ten sides, preferably from five to nine sides, particularly preferably six, seven or eight sides.

For good transmission of the signal within the probe, it is advantageous if the at least one layer of a conducting material on the first side of the base layer, which follows proximally the annular conductor structure as the feed line, comprises at least two elongate conductors which are spaced apart from one another and which are connected electrically to one another in the region of the connection to the annular conductor structure and in the region of the proximal end of the probe.

Simple handling for medical staff is facilitated if the probe has at its proximal end a connecting region for electrical and mechanical connection to a connecting cable, which is preferably in coaxial form.

The probe according to the invention is particularly reliable to use if the at least one layer of a conducting material on the first side of the base layer is connected as the exciter to the annular conductor structure and to the at least one elongate conductor in the form of the feed line for the annular conductor structure, and the layer of a conducting material on the second side of the base layer is connected as the earth.

The invention will be explained in greater detail below by means of exemplary embodiments shown in the drawings, in which.

Figure 1:
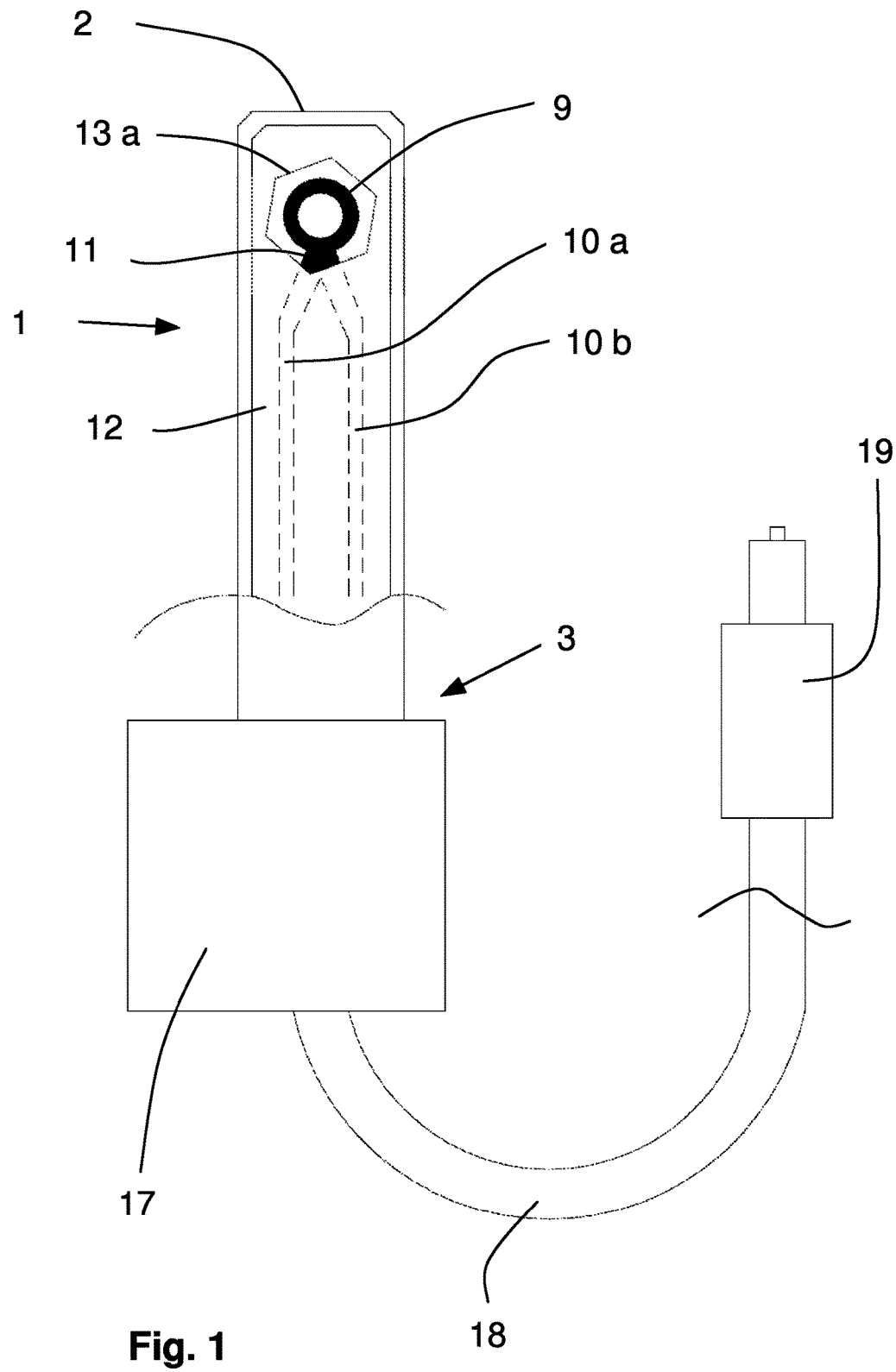
FIG. 1 shows a first embodiment of a probe according to the invention, partially cut away.

Frequency-dependent measurements in the range from a few kHz to about 100 GHz provide information about dynamic processes at molecular level.

At only a few tens of kHz, the skin effect and protection from high-frequency interference normally require the use of shielded coaxial cables. This requirement is not a problem for extracorporeal impedance measuring cells, in contrast to invasive probes, where the outside diameters of commercial coaxial cables, which are dictated by the available dielectrics, already prohibit use in catheters, for example. Unlike the measurement of blood cells by impedance spectroscopy in the higher kHz range, frequencies in the higher MHz range are required in the case of biomolecules. A probe for electrochemical impedance spectroscopy at such frequencies accordingly behaves in principle like an antenna.

A particular problem thereby is the available space for probes that are to be used invasively. In Gaetano Marrocco: The Art of UHF RFID Antenna Design: Impedance Matching and Size-Reduction Techniques, IEEE Antennas and Propagation Magazine, Vol. 50; No. 1, pages 66 ff, a number of proposals for reducing the size of antennas, in particular of multi-band antennas, are described.

Surprisingly, however, a configuration of a probe has been found by the inventors that permits electrochemical impedance spectroscopy at frequencies significantly above 100 MHz and nevertheless permits such small "antenna" structures that they can be used invasively.

In the various embodiments of a probe according to the invention shown by way of example in the figures, the same parts have been given the same reference numerals. The embodiments shown in the figures of a probe arrangement according to the invention for measuring biomolecules by means of electrochemical impedance spectroscopy first of all comprise the actual probe, designated generally by 1, having a distal end 2 and a proximal end 3.

Figure 2:
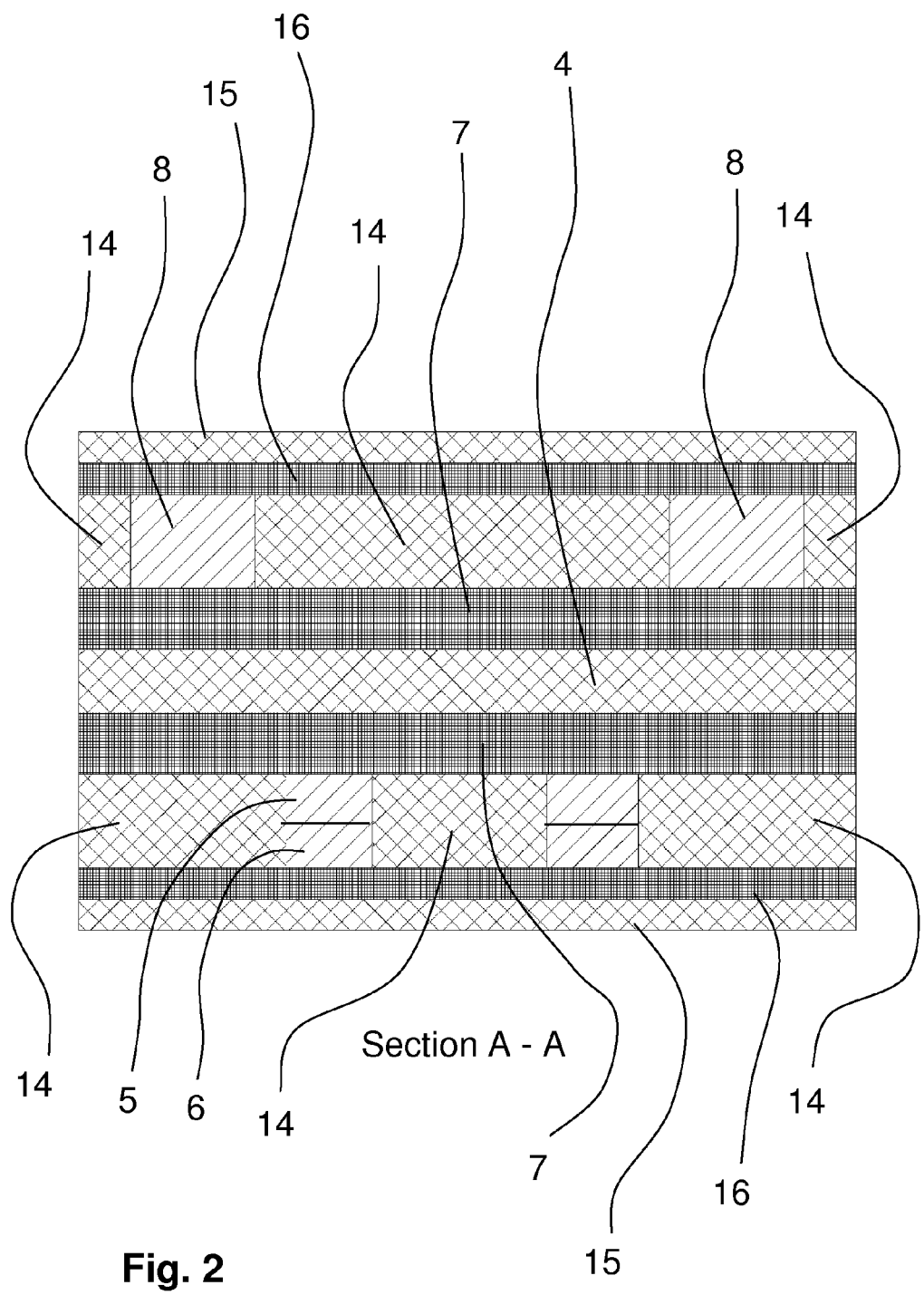
FIG. 2 shows a cross-sectional view through a probe according to the invention along the line A-A in FIG. 3.
Figure 3:
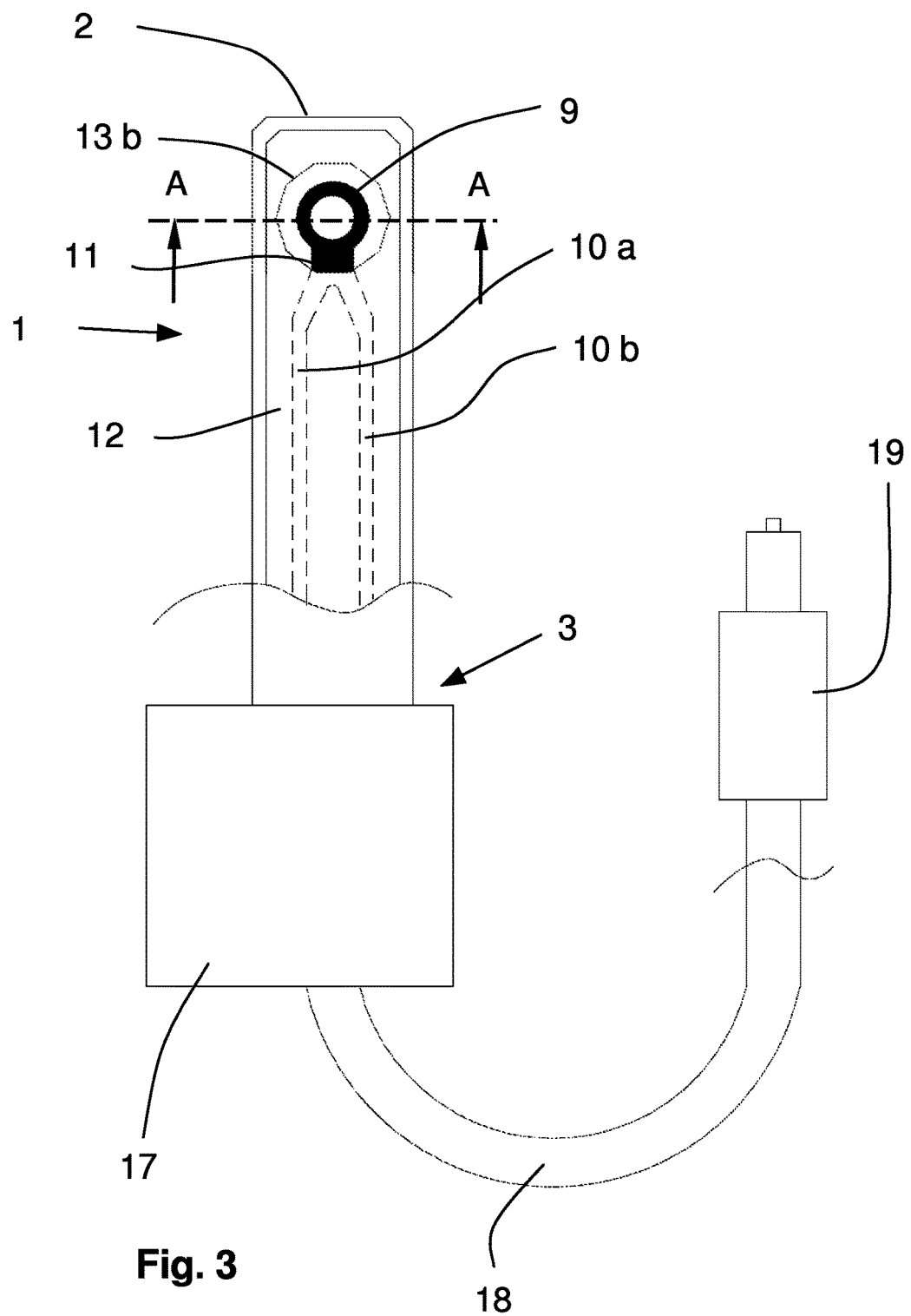
FIG. 3 shows a second embodiment of a probe according to the invention, partially cut away.
Figure 4:
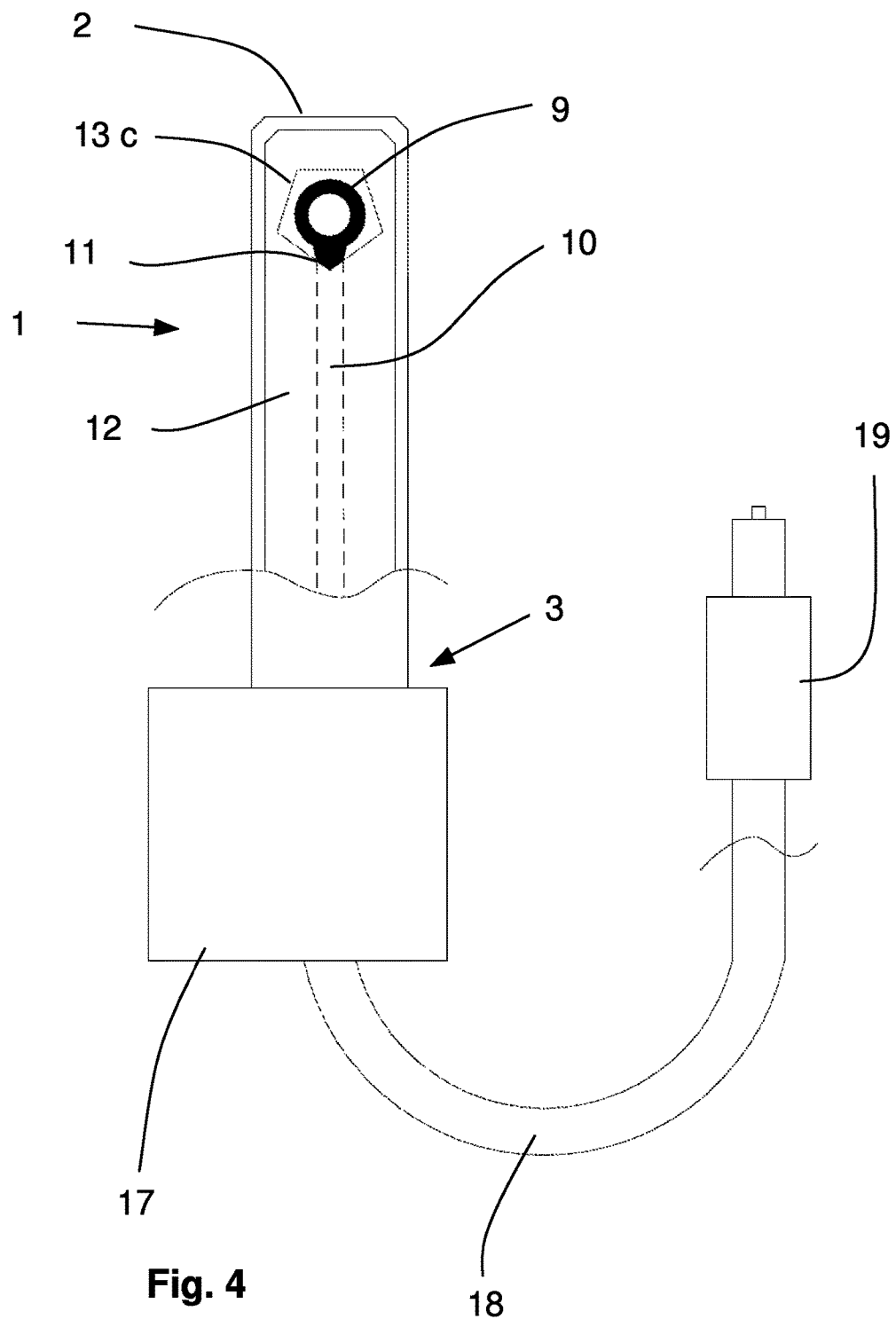
FIG. 4 shows a third embodiment of a probe according to the invention, partially cut away.
Figure 5:
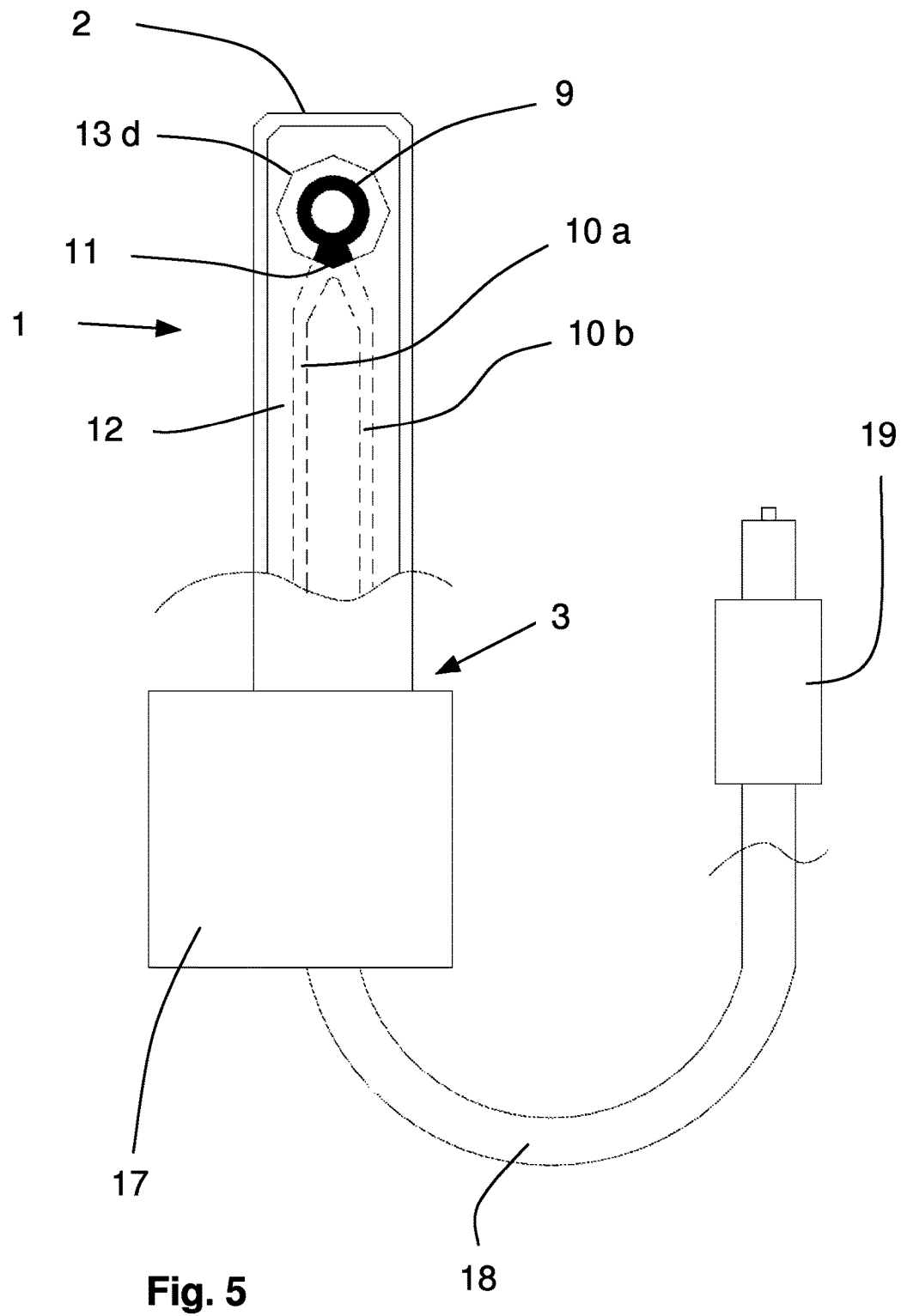
FIG. 5 shows a fourth embodiment of a probe according to the invention, partially cut away.

As can readily be seen in the cross-sectional view of FIG. 2 arranged transversely to the longitudinal extent of the probe, a suitable configuration of a probe 1 according to the invention comprises a central insulating layer, the base layer 4. The base layer 4 preferably consists of a material having a dielectric constant of less than 3.7 (IEC 60250, 1 MHz). Polyimide has been found to be particularly suitable. Although that material has a relatively high water absorption of approximately 2.8%, that material can be processed particularly easily in the production of a probe according to the invention, and reliable processes are available for processing the conducting layers and covering them with copper. Alternatively, flexible polyamide 6, polyamide 12, polyester film or PTFE (polytetrafluoroethylene) can be used.

On both sides of the base layer 4 there is applied a layer 8 of a conducting material. The conducting material is advantageously a copper alloy. A layer 8 thereby consists of a first ply 5 of a copper film and a second ply 6 applied to the first ply 5 by galvanic deposition. For the sake of clarity, the division into the first and second plies 5, 6 is shown only on the lower side of the base layer 5. Advantageously, the first ply 5 of copper is laminated on by means of an adhesion promoter layer 7 of an epoxy resin and then structured by a subtractive process known from the manufacture of printed circuit boards, for example by etching off unmasked regions. The first ply 5 can, however, also be formed by an additive process, for example by sputtering onto the adhesion promoter layer 7. The etching process can thereby be omitted, because the desired conductor structures in the copper ply 5 are already formed during sputtering. The second ply 6 of the layer of conducting material is advantageously formed by galvanic deposition of copper onto the structures formed in the first ply 5. The layer thickness of the conducting layer 8 that is required for use can thereby be produced in a simple manner.

Conventional electro copper, as is also employed for the manufacture of printed circuit boards, is advantageously used as the conducting material. However, it is also possible within the context of this invention to use any other conducting materials that are otherwise employed for conducting layers in the manufacture of printed circuit boards, in particular flexible printed circuit boards.

The conductor layer shown with the two plies 5 and 6 is formed into an annular conductor structure 9 in the region of the distal end 2 of the probe 1, as can better be seen in FIGS. 1 and 3 to 5. The annular conductor structure 9 is followed proximally by at least one elongate conductor 10 which is in the form of a feed line for the annular conductor structure 9 and extends to the proximal end 3 of the probe 1.

For good transmission of the signal within the probe 1, it is advantageous if the elongate conductor 10 comprises two elongate conductors 10a and 10b which are spaced apart from one another (see FIGS. 1, 3 and 5) and which are connected electrically to one another (not shown) in the region of the connection 11 to the annular conductor structure 9 and in the region of the proximal end 3 of the probe 1.

The layer 8 of a conducting material on the second side of the base layer 4 covers the predominant part of the base surface of the base layer 4 as the ground plane or earth 12, the layer 8 of a conducting material on the second side of the base layer 4 having in the region of the distal end 2 of the probe 1 a polygonal hole 13 which is arranged concentrically to the annular conductor structure 9. In the embodiment in FIG. 1, the hole 13 is a six-sided hole 13a, in the embodiment in FIG. 3 the hole 13 is a ten-sided hole 13b, in the embodiment in FIG. 4 the hole 13 is a five-sided hole 13c, and in the embodiment in FIG. 5 the hole 13 is an eight-sided hole 13d.

Each of the layers of a conducting material is embedded in an insulating material 14, preferably likewise in a polyimide such as that of the base layer 4.

On the side of the layers 5, 6, 8 of conducting material that is remote from the base layer 4 there is applied on the outside in each case an outer layer 15 of an insulating material by way of a further adhesion promoter layer 16. The material of the outer layers 15 advantageously corresponds to that of the base layer 4, and the material of the adhesion promoter layers 16 advantageously corresponds to that of the adhesion promoter layer 7.

For the purpose of better understanding, the probe 1 is shown in FIGS. 1 and 3 to 5 with part of the outer layer 15 and the adhesion promoter 16 removed, so that the ground or earth 12 can be seen and in particular the hole 13 is visible.

The structure according to the invention of the probe 1 on the one hand produces sufficient flexibility of the probe 1 that it is able to follow the bends of a catheter inserted into a blood vessel, and on the other hand produces sufficient stiffness that it is able to absorb the frictional forces that occur when the probe 1 is pushed into a catheter.

The structure shown with suitable and proven layer thicknesses of the individual layers gives an overall thickness of the probe 1 of about 175 µm. With a suitable width of the probe 1 of about 0.25 mm, a greatest cross-sectional extent of about 305 µm is obtained with an approximately rectangular cross-section. The probe 1 according to the invention thus fits into a catheter lumen having a size of only 1 F (which corresponds nominally to an inside diameter of about 318 µm)! It is accordingly possible in particular with the structure according to the invention to use a probe according to the invention in the side lumen of sizes from 1 F to a maximum of 2 F of multi-lumen catheters, as are frequently used for the care of intensive care patients. The rectangular cross-sectional contour of the probe 1 is thereby advantageous also in the case of a lumen having a round cross-section, because the contact surfaces between the probe 1 and the catheter wall are thereby minimised and insertion of the probe 1, which is usually about 30 cm long, into the catheter is facilitated.

For simple handling by medical staff, the probe 1 has at its proximal end 3 a connecting region, provided with a protective casing 17, for electrical and mechanical connection to a connecting cable 18 of coaxial form. The coaxial cable 18 advantageously has an impedance of 50 ohms and is provided with a BNC connector 19 for connection to a network analyser. The connecting region 17 can have a reinforcement of the probe 1 by means of a laminated epoxy resin circuit board and/or can be configured separably with an FFC cable bushing. In the latter case especially, the feed line 10 and the ground or earth 12 are exposed in that region and provided with an anti-corrosive coating, for example gold-plated.

For carrying out a measurement with a probe according to the invention, the probe is connected to a modern network analyser. For tests with a probe according to the invention it is possible to use, for example, a vectorial impedance meter which is able to measure the complex resistance of the probe over a wide frequency range. An instrument suitable for tests is obtainable as antenna analyser FA-VA3 from Box 73 Amateurfunkservice GmbH in Berlin. By wobbling through as large a relevant frequency range as possible, for example 70 MHz to 165 MHz, it is possible with the aid of such a network analyser, by signal evaluation of the absorption spectra of known biomolecules, such as lactate, to determine them qualitatively and quantitatively. In particular, changes in the concentration can easily be detected and where appropriate, for example if given threshold values are exceeded, an alarm can be emitted for medical staff.

The invention claimed is:

1. A probe for measuring biomolecules by electrochemical impedance spectroscopy, the probe having a distal end, a proximal end, a longitudinal extent, and a structure in a cross-section oriented transversely to the longitudinal extent, comprising:

a base layer of an insulating material having a first side and a second side which is remote from the first side, wherein on the first side of the base layer is at least one layer of a conducting material, and on the second side of the base layer is at least one layer of a conducting material, and on the side of the layers of conducting material that is remote from the base layer, on the outside, in each case an outer layer of an insulating material, wherein the at least one layer of a conducting material on the first side of the base layer is formed into an annular conductor structure in a region of the distal end of the probe, wherein the annular conductor structure is followed proximally by at least one elongate conductor which is in a form of a feed line for the annular conductor structure and extends to the proximal end of the probe, wherein the at least one layer of a conducting material on the second side of the base layer covers a predominant part of a base surface of the base layer, wherein the at least one layer of a conducting material on the second side of the base layer has in the region of the distal end of the probe a polygonal hole which is arranged concentrically to the annular conductor structure, and wherein the polygonal hole is at least sufficiently large that the annular conductor structure is not covered by the conducting material on the second side of the base layer that surrounds the hole.

2. The probe according to claim 1, wherein each of the layers of a conducting material is embedded in an insulating material.

3. The probe according to claim 1, wherein the conducting material of each of the layers of a conducting material is a copper alloy.

4. The probe according to claim 1, wherein the insulating material of the base layer is a same material as the outer layers and/or of an embedding material of the layers of a conducting material.

5. The probe according to claim 1, wherein the insulating material of the base layer is a material having a dielectric constant of less than 3.7.

6. The probe according to claim 1, wherein the insulating material of the base layer and/or the outer layers, and/or an embedding material of the layers of a conducting material is a polyimide.

7. The probe according to claim 1, wherein a largest diameter of the polygonal hole is not more than 1.5 times a largest diameter of the annular conductor structure.

8. The probe according to claim 1, wherein the polygonal hole has from four to ten sides.

9. The probe according to claim 1, wherein the at least one layer of a conducting material on the first side of the base layer, which follows proximally the annular conductor structure as the feed line, comprises at least two elongate conductors which are spaced apart from one another and which are connected electrically to one another in a region of the connection to the annular conductor structure and in a region of the proximal end of the probe.

10. The probe according to claim 1, wherein the probe has at the proximal end a connecting region for electrical and mechanical connection to a connecting cable.

11. The probe according to claim 1, wherein the at least one layer of a conducting material on the first side of the base layer is connected as an exciter to the annular conductor structure and to the at least one elongate conductor in the form of the feed line for the annular conductor structure, and the layer of a conducting material on the second side of the base layer is connected as earth.

12. The probe according to claim 1, wherein each layer of a conducting material has a first ply of a copper film and a second ply applied to the first ply by galvanic deposition.

13. A probe for measuring biomolecules by electrochemical impedance spectroscopy, the probe having a distal end, a proximal end, a longitudinal extent, and a structure in a cross-section oriented transversely to the longitudinal extent, comprising:
   a base layer of an insulating material having a first side and a second side which is remote from the first side,
   wherein on the first side of the base layer is at least one layer of a conducting material, and on the second side of the base layer is at least one layer of a conducting material, and on the side of the layers of conducting material that is remote from the base layer, on the outside, in each case an outer layer of an insulating material,
   wherein the at least one layer of a conducting material on the first side of the base layer is formed into an annular conductor structure in a region of the distal end of the probe,
   wherein the annular conductor structure is followed proximally by at least one elongate conductor which is in a form of a feed line for the annular conductor structure and extends to the proximal end of the probe,
   wherein the at least one layer of a conducting material on the second side of the base layer covers a predominant part of a base surface of the base layer,
   wherein the at least one layer of a conducting material on the second side of the base layer has in the region of the distal end of the probe a polygonal hole which is arranged concentrically to the annular conductor structure, and
   wherein the at least one layer of a conducting material on the first side of the base layer, which follows proximally the annular conductor structure as the feed line, comprises at least two elongate conductors which are spaced apart from one another and which are connected electrically to one another in a region of the connection to the annular conductor structure and in a region of the proximal end of the probe.

14. The probe according to claim 13, wherein each of the layers of a conducting material is embedded in an insulating material.

15. The probe according to claim 13, wherein the conducting material of each of the layers of a conducting material is a copper alloy.

16. The probe according to claim 13, wherein the insulating material of the base layer is a same material as the outer layers and/or of an embedding material of the layers of a conducting material.

17. The probe according to claim 13, wherein the insulating material of the base layer is a material having a dielectric constant of less than 3.7.

18. The probe according to claim 13, wherein the insulating material of the base layer and/or the outer layers, and/or an embedding material of the layers of a conducting material is a polyimide.

19. The probe according to claim 13, wherein the polygonal hole is at least sufficiently large that the annular conductor structure is not covered by the conducting material on the second side of the base layer that surrounds the hole.

20. The probe according to claim 13, wherein the polygonal hole has from four to ten sides.

21. The probe according to claim 13, wherein the probe has at the proximal end a connecting region for electrical and mechanical connection to a connecting cable.

22. The probe according to claim 13, wherein the at least one layer of a conducting material on the first side of the base layer is connected as an exciter to the annular conductor structure and to the at least one elongate conductor in the form of the feed line for the annular conductor structure, and the layer of a conducting material on the second side of the base layer is connected as earth.

23. The probe according to claim 13, wherein each layer of a conducting material has a first ply of a copper film and a second ply applied to the first ply by galvanic deposition.

24. The probe according to claim 13, wherein a largest diameter of the polygonal hole is not more than 1.5 times a largest diameter of the annular conductor structure.

* * * * *